United States Patent [19]

Sasser et al.

[11] Patent Number: 4,705,748

[45] Date of Patent: * Nov. 10, 1987

[54] ANTIGEN ASSOCIATED WITH EARLY DETECTION OF MAMMALIAN PREGNANCY

[75] Inventors: R. Garth Sasser, Moscow; William C. Hamilton, Emmett, both of Id.

[73] Assignee: Idaho Research Foundation, Inc., Moscow, Id.

[*] Notice: The portion of the term of this patent subsequent to Nov. 19, 2002 has been disclaimed.

[21] Appl. No.: 794,932

[22] Filed: Nov. 4, 1985

Related U.S. Application Data

[63] Continuation of Ser. No. 516,173, Jul. 21, 1983, Pat. No. 4,554,256.

[51] Int. Cl.[4] ................. G01N 33/531; G01N 33/542
[52] U.S. Cl. ......................................... 435/7; 436/510; 436/518; 436/520; 436/525; 436/536; 436/540; 436/542; 436/543; 436/544; 436/545; 436/546; 436/547; 436/548; 436/804; 436/814; 436/815
[58] Field of Search ................ 436/510, 536, 542–545, 436/804, 814, 815, 537, 518, 520, 546, 525, 540, 547, 548; 435/7; 424/105

[56] References Cited

U.S. PATENT DOCUMENTS

| | | | |
|---|---|---|---|
| 3,892,841 | 7/1975 | Barg, Jr. | 436/805 |
| 3,911,108 | 10/1975 | Singh | 424/86 |
| 4,313,871 | 2/1982 | Bahl | 424/85 |
| 4,325,866 | 4/1982 | Bohn | 260/112 B |
| 4,329,213 | 5/1982 | Elwing | 436/516 |
| 4,402,872 | 9/1983 | Bohn | 260/112 R |
| 4,489,166 | 12/1984 | Joshi | 436/510 |
| 4,554,256 | 11/1985 | Sasser et al. | 436/510 |

OTHER PUBLICATIONS

Ivani, K. A. et al, Biol. Reprod. 30(1):51, Abstract 42, (1984).
Bohn, H. et al, *Proteins in Body Fluids, Amino Acids, and Tumor Markers: Diagnostic and Clinical Aspects,* pp. 333–374, (1983); Alan R. Liss, Inc., N.Y., N.Y., "Placental and Pregnancy-Related Proteins." Review.
Bolton, A. E. et al, Clinica Chemica Acta 135:283–291 (1983).
Butler, J. E. et al, Biology of Reproduction, 26:925–933 (1982).
O'Sullivan, M. J. et al., Clin. Exper. Immunol. 48:279–287 (1982).
Klopper, A., Placental Proteins, 1:77–89 (1980), Review.
Butler, J. E. et al., Journal of Animal Sciences 51(1):266, Abstract 390, (1980).
Sasser, R. G. et al, Journal of Animal Sciences, 49(1):333, Abstract 472 (1979).
Lai, P. C. W. et al, Biochmica et Biophysica Acta 535:138–149 (1978).
Hayden, T. J. et al, J. Endocrinology 80:68P (1979).
Roberts, Glyn P. et al, Biochimica et Biophysica Acta 446:69–76 (1976).

*Primary Examiner*—Margaret Moskowitz
*Attorney, Agent, or Firm*—Bertram I. Rowland

[57] ABSTRACT

Early pregnancy can be determined by detection of a protein in milk, which protein is associated with the placental membrane. The protein is characterized by having an approximate molecular weight of 47,000 to 53,000 and an isoelectric point of from about 4.0–4.4.

4 Claims, No Drawings

ANTIGEN ASSOCIATED WITH EARLY DETECTION OF MAMMALIAN PREGNANCY

CROSS-REFERENCE TO RELATED APPLICATIONS

This application is a continuation of application Ser. No. 516,173, filed July 21, 1983, now U.S. Pat. No. 4,554,256, which disclosure is incorporated herein by reference.

BACKGROUND OF THE INVENTION

1. Field of the Invention

There is a continuing interest in determining physiological compounds which are used for regulation of cellular functions. As these compounds are discovered and studied, a better understanding of the way organs function and communicate is obtained.

Pregnancy requires communication between the fetus and the host. The placenta serves as a barrier for transmission of various products produced by the fetus and/or the mother. Particularly, the bovine fetus is normally protected from the maternal immune system.

In many situations, particularly with domestic animals, which are frequently bred by artificial insemination, there is substantial interest in being able to detect at an early date the existence of pregnancy.

2. Description of the Prior Art

Butler et al., Biology of Reproduction (1982) 26:925–933 describes the detection and partial characterization of two bovine pregnancy-specific proteins. Butler et al., 1980 72nd Annual Meeting of the American Society of Animal Science, July 27–30, 1980, reported the isolation of two pregnancy-associated proteins from bovine placental membranes. Sasser et al., J. Anim. Sci. (1979) 49:333, Suppl. 1 (Abstract) reported placental-associated antigens during early pregnancy in the cow.

SUMMARY OF THE INVENTION

Early pregnancy can be detected in physiological fluids external to the fetus by the presence of Protein B, characterized by having a molecular weight in the range of 47 to 53 kilodaltons (kd), an isoelectric point in the range of about 4.0–4.4 and isolatable from placental membrane homogenate. Antibodies to Protein B can be prepared by conventional techniques to be used to detect the presence of Protein B in the mammalian fluid, e.g. serum, as diagnostic of pregnancy.

DESCRIPTION OF THE SPECIFIC EMBODIMENTS

Methods and compositions are provided for determining pregnancy in mammals, particularly domestic animals. Detection of the presence of Protein B in physiological fluids external to the fetus, particularly the serum of the female is positive for the occurrence of pregnancy and fetal presence. Protein B is characterized by having a molecular weight in the range of about 47 to 53 kd, an isoelectric point in the range of about 4.0–4.4 and isolatable from placental membrane homogenates.

The physiological fluids of interest are serum, milk and urine, particularly serum. Protein B may be isolated in accordance with the following procedure. The placental membranes from embryos of at least about 12, usually at least about 20, days of age are isolated, the membranes minced and homogenized and the solids separated and the supernatant collected. Desirably, the temperature is maintained at or below about 10° C., preferably below about 5° C.

To the supernatant, generally at a temperature below about 5° C., usually between about 0°–5° C., is added ammonium sulfate and the fraction precipitating between 50% to 65% saturation with ammonium sulfate isolated. The precipitate is dialyzed against an appropriate buffer, e.g. Tris-HCl, at a physiological pH, e.g. about 7.5, in a dialysis tube with an exclusion limit under 15,000 daltons (d). Dialysis is conveniently carried out for about 48 h. The dialysate is then concentrated and chromatographed on a cationic ion exchange column. Conveniently, an amino substituted column is employed, particularly a diethylaminoethylcellulose column is employed. The elution is performed employing as the eluent a buffered aqueous solution at about physiologic pH, e.g. 7.5, followed by a linear salt gradient, with a final cut off of about 0.3M NaCl. Fractions are isolated and monitored by absorption at 280 nm. Once antibodies are available, Protein B can be monitored by an appropriate immunoassay.

The Protein B may be further purified by gel filtration using Bio-Gel A-0.5 m using a convenient buffer at pH 7.5 and 0.1 M NaCl. The gel has an exclusion limit of 500 kd and a fractionation range of 10 to 500 kd. The proteins may be concentrated by ultrafiltration.

The Protein B concentrate can be used to prepare antibodies, either mono- or polyclonal for use in immunoassays. Different techniques will be employed for the production of mono- or polyclonal antibodies. For monoclonal, conveniently, a mouse may be injected with the purified antigen, followed by one or more injections at about 2 week intervals in combination with conventional adjuvants to provide for the immune response. The mouse may then be sacrificed, the spleen isolated, and fused in accordance with conventional techniques with an appropriate fusion partner, the resulting viable hybridomas are isolated, cloned, and screened for specificity to Protein B. See for example, U.S. Pat. Nos. 4,364,937 and 4,381,292.

For polyclonal antisera, various domestic animals may be employed other than the source of the placental membrane. The domestic animal is injected with an appropriate amount of the protein in conjunction with conventional adjuvants and the injection repeated at 2 to 3 week intervals to hyperimmunize the host. The host may then be bled and the immunoglobulin precipitated and purified by conventional techniques. See for example, U.S. Pat. Nos. 3,822,245 and 3,817,837.

Protein B may be used for detection of pregnancy in the host as well as other closely related mammals, due to immunogenic cross reactivity. Of particular interest for pregnancy detection are domestic animals, such as farm animals and pets. These include families such as bovine, equine, porcine, ovine, canine, feline, and the like. The test finds particular application with mammals of lower order than primate.

The antibodies may be used in a wide variety of conventional immunoassays. The antibodies may be labeled or unlabeled, depending upon the particular test. For example, in hemagglutination tests, the antibody need not be labeled but may be bound to erythrocytes or other particle. Alternatively, in other assays, the antibodies may be conjugated to radionuclides, e.g. $^{125}$I, enzymes, fluorescers, metal particles, fluorescent particles, substrates, enzyme inhibitors, chemiluminescers, or other label which provides a detectable signal. Alternatively, Protein B or a cross reacting fragment thereof may be labeled for detection of Protein B. The assay may be carried out employing a heterogeneous technique (requiring a separation step) or a homogeneous technique (not requiring a separation step). Alternatively, various supports can be used where the assay chemistry occurs on a support.

In carrying out the assay, the reagents and sample are normally combined under conditions which allow for detection of the presence of immunological complexes of antigen and antibody. By measuring the amount of such complex, one can relate this amount to the amount of Protein B in the sample.

Illustrative of immunoassay techniques are the methods disclosed in U.S. Pat. Nos. 3,654,090; 3,817,837; 3,853,467; 3,853,987; 3,911,096; 3,949,064; 3,998,943; and 4,012,494. Various immunologic laboratory tests are described In Basic and Clinical Immunology, Stites et al., 4th ed., Lang Medical Publications, Los Altos, Calif., 1982, pp. 325.

For convenience, the reagents are frequently provided in kits, where the labeled reagent is present in conjunction with buffer, stabilizers, excipients and any additional reagents necessary for the detection of the signal for the performance of the assay. Furthermore, the various materials are carefully weighed to ensure that upon dilution into a predetermined volume, the concentration is optimized for sensitivity in the range of interest for Protein B.

Depending upon the assay, either the antibody or Protein B may be labeled. Where Protein B is labeled, the antibody will also be included, either combined with or separate from the labeled antigen. Alternatively, the antibody or antigen, usually the antibody, may be bound to a support where the antigen present in the sample will serve as a bridge for binding labeled antibody to the support. The kit would then include the support containing the conjugated antibody and labeled antibody for combining with the sample.

It is found that the presence of a serum concentration significantly different from buffer control, i.e. without Protein B, is indicative of pregnancy. Preferably, the cut off for a positive test should be at least about 0.15, more preferably at least about 0.25 ng/ml. Monitoring may be initiated at 5 days after insemination, usually at least about 10 days after insemination. By 20 days after insemination, Protein B should be greater than about 0.1 ng/ml concentration in the serum.

The following examples are offered by way of illustration and not by way of limitation.

EXPERIMENTAL

Materials and Methods

Embryos were collected from dairy and beef cows at slaughter. Ages of the embryos were estimated by crown-rump measurement (Rexroad et al., *J. Dairy Sci.* (1974) 57:346). Placental membranes were removed from embryos between 16 and 280 days of gestation and frozen at $-20°$ C. After finely mincing by shaving with a razor blade, the preparation was homogenized in a commercial Waring blender and the preparation centrifuged at $10,000 \times g$ for 30 min at 4° C.

The resulting supernatant was placed in an ice bath and the fraction which precipitated between 50 and 65% saturation with ammonium sulfate isolated and dissolved in 0.01M Tris-HCl buffer, pH 7.5 at 4° C. After dialysis for 48 h at 4° C. against this buffer in dialysis tubing with an exclusion limit of 12-13 kd (the buffer changed at 24 h) the protein content was determined and the dialysate concentrated to approximately 25 mg/ml of protein with an Amicon model 202 ultrafiltration cell using an UM 10 membrane (exclusion limit 10 kd).

The protein was further purified by ion exchange chromatography at 4° C. on a column (1.6×30 cm) of diethylaminoethylcellulose (DE52; Whatman, Inc., Clifton, N.J.). Approximately 150 g of protein were loaded onto the column in 0.01M Tris-HCl buffer, pH 7.5, at a rate of 1 ml/min and after elution of unbound proteins, a linear salt gradient of 0.0–0.3M NaCl was then applied over the next 3.3 h. Fractions (5 ml) were collected and the elution of protein was monitored by absorbance at 280 nm. Fractions of antigenic activity were pooled, frozen and stored at $-20°$ C.

Gel filtration was performed at 4° C. using a column (2.2×90 cm) of Bio-Gel A-0.5m (Bio-Rad Labs., Richmond, CA) equilibrated and eluted with 0.1M NaCl, 0.01M Tris-HCl (pH 7.5). The gel has an exclusion limit of 500 kd and a fractionation range from 10 to 500 kd. Pregnancy-specific proteins obtained from ion exchange chromatography were concentrated by ultrafiltration to approximately 15 mg/ml of protein and 4 ml were loaded onto the column. Fractions (3.5 ml) containing pregnancy-specific proteins were pooled, frozen and stored at $-20°$ C. The molecular weights of the pregnancy-specific proteins were estimated with gel filtration by comparing the $K_{av}$ of the proteins to the $K_{av}$ of globular protein standards (Pharmacia Fine Chemicals, Piscataway, N.J.).

Two hundred micrograms of Protein B obtained as described above conjugated to tetanus toxoid (Golub et al., *J. Immunol.* (1968) 100:133) were dissolved in 1 ml of distilled water and emulsified with an equal volume of Freund's complete adjuvant was injected intradermally along the back at approximately 30 sites of New Zealand white rabbits weighing 2 to 3 kg each. (Vaitukatis et al., *J. Clin. Edocrinol. Metab.* (1971) 33:988-991.) Similarly, unconjugated antigen emulsified with Freund's incomplete adjuvant was administered at 3 week intervals for 9 weeks. Following the second injection, blood was collected weekly from an ear vein, allowed to clot for 48 h at 4° C., the sera removed and stored at $-20°$ C.

The antisera was used at a dilution of 1:60,000 in 1:400 normal rabbit serum EDTA-phosphate buffered saline and bound 40% of labeled hormone in the absence of unlabeled hormone. The rabbit gammaglobulin antisera was developed in a ewe as described by Niswender et al., *Endocrinology* (1969) 34:1166.

Radioiodination of Protein B was accomplished using the method of Greenwood et al., *Biochem. J.* (1963) 89:114. Free iodine was separated from radioactive Protein B by chromatography on a 1×12 cm column of Bio-Gel P-60. The specific activity of Protein B $^{125}$I was 90-110$\mu$Ci/$\mu$g. Assay procedures were those described by Niswender et al. (1969) supra for assay of luteinizing hormone.

Isoelectric focusing was performed in a Bio-Rad Labs' model 1415 electrophoresis cell with a granulated gel bed of 30×11×0.8 cm at 9 watts for 20 h using ampholytes with an operating range of pH 3.0–5.0 (Bio-Lyte 3/5), with a gel containing 2% ampholytes. Approximately 450 mg of the placental extract which had been treated with ammonium sulfate (as described above) were applied to the gel bed and focused gels divided into 36 equal fractions and the pH of these determined. Fractions were eluted in 10 ml columns with 10 ml of PBS (pH 7.0). The isoelectric point for Protein B was found to be between pH 4.0 and 4.4.

The molecular weight was determined by gel filtration as described above. Protein B was located in fractions 49-57 giving an estimated molecular weight of 47-53 kd.

In the radioimmunoassay, the inhibition curve ranged from 3 to 92% of buffer control with 20-0.16 ng Protein B per tube. The assay was sensitive to 0.07 ng per tube. At a dilution of 1:200, 50μl of supernatant of bovine placental homogenate inhibited binding at 4%. Cross reactivity was not observed with a number of hormones of the placenta and the pituitary. These hormones included bovine thyrotropin, growth hormone and prolactin. Bovine luteinizing hormone and ovine placental lactogen caused some inhibition at substantially higher concentrations than an equivalent weight amount of Protein B. For example, 1 μg of luteinizing hormone was equivalent to 0.37 ng Protein B.

An extensive study was carried out with 102 beef cows which had bred between 27 and 96 days prior to the first diagnosis (described below). A veterinarian performed a diagnosis by rectal palpation. At the same time, a blood sample was drawn from the jugular vein of each cow. Plasma from the blood was assayed by radioimmunoassay as described above. Animals that were diagnosed non-pregnant were reexamined by the same veterinarian 50 days after the first examination. Then, a blood sample was drawn for a second radioimmunoassay for Protein B. The assays had a sensitivity of 188 pg/ml and 137 pg/ml plasma, respectively, and values above these levels within each assay were reported as positive. On the first occasion, the two diagnoses agreed in 90 of 102 cases and disagreed in 12 cases. Rectal palpation showed that 15 cows were not pregnant, while RIA diagnosis showed that 3 were not pregnant.

The 15 cows diagnosed non-pregnant by rectal palpation were reexamined. Five of the 15 cows were diagnosed non-pregnant by rectal palpation. These 5 animals were slaughtered and the reproductive tracts were examined for presence of a conceptus. One of the 5 cows was pregnant. This one had previously been diagnosed pregnant by radioimmunoassay. Another of the 5 had been diagnosed pregnant by the first and non-pregnant by the second radioimmunoassay and non-pregnant by both palpations. Examination of the reproductive tract at slaughter showed the animal was not pregnant. It is possible that an embryo was present early but was later aborted or reabsorbed. The other 3 animals were diagnosed non-pregnant at each time by both methods.

It is evident from the above results, that a simple, rapid technique is provided for determining pregnancy of a mammal at early stages in the fetal development. Since Protein B is found in the serum of the mother and is capable of crossing the placental barrier, the presence of Protein B in a non-pregnant host may be used for diagnosis of physiologic aberration.

Although the foregoing invention has been described in some detail by way of illustration and example for purposes of clarity of understanding, it will be obvious that certain changes and modifications may be practiced within the scope of the appended claims.

What is claimed is:

1. A method for detecting pregnancy in a domestic animal host producing a protein cross-reactive with Protein B, which comprises combining milk from said host with antibody which specifically binds to Protein B, said Protein B being characterized as having a molecular weight in the range of about 47-53 kD, an isoelectric point in the range of about 4.0-4.4 and isolatable from bovine placental membrane homogenates; and detecting the presence of an immunological complex between said antibody to Protein B and an antigen in milk from said host, wherein complex formation is indicative of pregnancy in said host.

2. A method according to claim 1, wherein said complex between said antibody to Protein B and said antigen in milk comprises a label capable of providing a detectable signal.

3. A method according to claim 1, wherein antibody which specifically binds to Protein B is conjugated with a label capable of providing a detectable signal.

4. A method according to claim 1, wherein said host is bovine.

* * * * *